(12) United States Patent
Nam et al.

(10) Patent No.: US 6,569,528 B2
(45) Date of Patent: May 27, 2003

(54) AMPHIPHILIC BIODEGRADABLE BLOCK COPOLYMERS AND SELF-ASSEMBLED POLYMER AGGREGATES FORMED FROM THE SAME IN AQUEOUS MILIEU

(75) Inventors: Yoon Sung Nam, Kyunggi-do (KR); Hyung Seok Kang, Kyunggi-do (KR); Sang Hoon Han, Kyunggi-do (KR); Ih Seop Chang, Kyunggi-do (KR)

(73) Assignee: Pacific Corporation, Seoul (KR)

( * ) Notice: Subject to any disclaimer, the term of this patent is extended or adjusted under 35 U.S.C. 154(b) by 0 days.

(21) Appl. No.: 10/173,728

(22) Filed: Jun. 19, 2002

(65) Prior Publication Data

US 2003/0009004 A1 Jan. 9, 2003

(30) Foreign Application Priority Data

Jun. 23, 2001 (KR) .......................................... 2001-36048

(51) Int. Cl.[7] ............................................... B32B 15/02
(52) U.S. Cl. ........................ 428/402; 528/354; 528/361; 525/450; 525/540
(58) Field of Search ................................. 528/354, 361; 525/450, 540; 428/402

(56) References Cited

PUBLICATIONS

A. V. Kabanov et al., A New Class of Drug Carriers: Micelles of Poly(oxyethylene)–poly(oxypropylene) Block Copolymers as Microcontainers for Drug Targeting from Blood in Brain, Journal of Controlled Release, 22, 141~158, 1992.

C. Allen et al., Polycaprolactone—b–poly(ethylene oxide) Copolymer Micelles as a Delivery Vehicle for Dihydrotestosterone, Journal of Controlled Release, 63, 275~286, 2000.

T. Inoue et al., An AB Block Copolymer of Oligo(methyl methacrylate) and Poly(acrylic acid) for Micellar Delivery of Hydrophobic Drugs, Journal of Controlled Release, 51, 221~2229, 1998.

A. Harada et al., Formation of Polyion Complex Micelles in an Aqueous Milieu from a Pair of Oppositely–Charged Block Copolyers with Poly(ethylene glycol) Segments, Macromolecules, 28, 5294~5299, 1995.

A. Harada et al., Novel Polyion Complex Micelles Entrapping Enzyme Molecules in the Core: Preparation of Narrowly–Distributed Micelles from Lysozyme and Poly(ethylene glycol)—Poly(aspartic acid) Block Copolymer in Aqueous Medium, Macromolecules, 31, 288~294, 1998.

K. Yu et al., Multiple Morphologies in Aqueous Solutions of Aggregates of Polystyrene–block–poly(ethylene oxide) Diblock Copolymers, Macromolecules, 29, 6359~6361, 1996.

B. M. Discher et al., Polymersomes: Tough Vesicles Made from Diblock Copolymers, Science, 248, 1143~1146, 1999.

L. Zhang et al., Multiple Morphologies of "Crew–Cut" Aggregates of Polystyrene–b–poly(acrylic acid) Block Copolymers, Science, 268, 1728~1731, 1995.

(List continued on next page.)

*Primary Examiner*—Samuel A. Acquah

(57) ABSTRACT

There are provided amphiphilic biodegradable block copolymers comprising polyethylenimine (PEI) as a hydrophilic block and aliphatic polyesters as a hydrophobic block, which can form various size of polymer aggregates and have very low critical micelle concentration, approximately $10^{-3}$ g/l in comparison with low-molecular-weight micelle, and self-assembled polymer aggregates formed from the block copolymers in aqueous milieu, which can be applied to solubilization of insoluble drug and a delivery system of proteins, genes or drugs.

19 Claims, 9 Drawing Sheets

OTHER PUBLICATIONS

L. Zhang et al., Ion–Induced Morphological Changes in "Crew–Cut" Aggregates of Amphiphilic Block Copolymers, Science, 272, 1777~1779, 1996.

L. Zhang et al., Morphogenic Effect of Added Ions on Crew–Cut Aggregates of Polystyrene–b–poly(acrylic acid) Block Copolymer in Solutions, Macromolecules, 29, 8805~8815, 1996.

C. Allen et al., Nano–Engineering Block Copolymer Aggregates for Drug Delivery, Colloids and Surfaces B: Biointerfaces, 16, 3~27, 1999.

R. Gref et al., Biodegradable PEG–Coated Stealth Nanospheres, Proceed. Intern. Symp. Control. Rel. Bioat. Mater., 20, 131~132, 1993.

G. Kwon et al., Micelles Based on AB Block Copolymers of Poly(ethylene oxide) and Poly(B–benzyl L–aspartate), Langmuir, 9, 945~949, 1993.

FIGURES

AMPHIPHILIC BIODEGRADABLE BLOCK COPOLYMERS AND SELF-ASSEMBLED POLYMER AGGREGATES FORMED FROM THE SAME IN AQUEOUS MILIEU

BACKGROUND OF THE INVENTION,

1. Field of the Invention

The present invention relates generally to amphiphilic biodegradable block copolymers and self-assembled polymer aggregates formed from the same in aqueous milieu. More particularly, the present invention relates to amphiphilic biodegradable block copolymers comprising polyethylenimine (PEI) as a hydrophilic block and aliphatic polyesters as a hydrophobic block, and self-assembled polymer aggregates formed from the block copolymers in aqueous milieu.

2. Description of the Related Arts

Recently, nanostrucured materials have received much attention as a potentially effective drug carrier. Therefore, various amphiphilic polymers comprising both a hydrophobic block and a hydrophilic block have been synthesized in order to develop effective nanostructures. In aqueous milieu, the hydrophobic compartment of an amphiphilic polymer has a tendency to self-assemble in order to avoid water and to minimize free interfacial energy of the system. By this hydrophobic interaction, the amphiphilic polymers form self-assembled aggregates in aqueous milieu. In addition, the hydrophilic blocks are uniformly dissolved in aqueous milieu and thereby the aggregates maintain a thermodynamically stable structure.

As compared with conventional low-molecular-weight micelles, polymer aggregates can form a more stable structure by chain entanglement and crystallinity of polymers, which is the reason why synthetic polymers have been extensively used as a material for drug delivery vehicles. Particularly, because the formed structure is uniform and nano-scale, it can be applied as a targetable drug delivery system, a carrier micelle for solubilizing insoluble drugs, and a gene delivery system.

These amphiphilic polymers exhibit various properties depending on their component blocks. For example, physicochemical properties of amphiphilic polymers and structures formed therefrom are determined by a molecular weight of the polymer, a ratio of hydrophilic/hydrophobic blocks, rigidity of blocks, affinity between blocks, molecular structure of blocks, charge density of a hydrophilic block, addition of ligands, etc.

In connection with a drug delivery system, many studies have been conducted on hydrophilic polymers. Hydrophilic polymers such as poly(ethylene oxide) (PEO) or poly(ethylene glycol) (PEG) have an excellent biocompatibility. In particular, there are many reports regarding the addition of poly(ethylene oxide) into various hydrophobic blocks.

For example, R. Langer of MIT synthesized polymer nanoparticles comprising polyethylene oxide as a hydrophilic block and biodegradable polyester as a hydrophobic block. The polyesters such as polylactide or poly(D,L-lactide-co-glycolide) was approved as a biodegradable and biocompatible polymer for clinical uses by Food & Drug Administration (FDA) in USA. In this case, we can observe that poly(ethylene oxide) drifts to the surface of nanoparticles by phase separation and drug concentration effused in blood increases in comparison with that case when polymer particles without poly(ethylene oxide) was used[R. Gref, Y. Minamitake, M. T. Peracchia, V. Trubeskoy, A. Milshteyn, J. Sinkule, V. Torchilin, R. Langer, *Int. Symp. Controlled Release Mater.*, 20, 131 (1993)].

Additionally, there have been reported the preparation of self-assembled polymer aggregates using poly(ethylene oxide) as a hydrophilic block, and as for a hydrophobic block, for example, using poly($\beta$-benzyl-L-aspartate) [G. S. Kwon, M. Naito, M. Yokoyama, T. Okano, Y.Sakurai, K. Kataoka, *Langmuir*, 9, 945 (1993)]; using poly(propylene oxide) [A. V. Kabanov, E. V. Batrakova, N. S. Neiknubanov, et al. *Journal of Controlled Release*, 22, 141 (1992)]; using poly($\epsilon$-caprolactone) [C. Allen, J. Han, Y. Yu, D. Maysinger, A. Eisenberg, *Journal of Controlled Release*, 63, 275 (2000)]; using oligo-methacrylate [T. Inoue, G. Chen, K. Nakamae, A. S. Hoffman, *Journal of Controlled Release*, 51, 221 (1998)]; etc.

Recently, there have been reported the preparation of polymer aggregates using ionic interactions. K. Kataoka et al. proposed a novel concept of polymer aggregates, "polyion complex (PIC) micelles" formed by ionic bonding between polymers having counter ions, by using both poly(ethylene oxide)-poly(L-lysine) block copolymer and poly(ethylene oxide)-poly(L-aspartate) block copolymer [A. Harada and K. Kataoka, *Macromolecules*, 28, 5294 (1995)]. By using this concept, they reported that lysozyme, which is a protein having an isoelectric point of 11 and thereby has positive charge, is successfully loaded within polymer micelles [A. Harada and K. Kataoka, *Macromolecules*, 31, 288 (1998)].

In addition to core-shell type polymer micelles using poly(ethylene oxide), there have been many concerns on structures such as cylindrical micelles, hollow vesicles, hollow hoops, etc. Adi Eisenberg (McGill University in Canada) reported various types of polymer aggregates using poly(ethylene oxide)-polystyrene copolymer [K. Yu and A. Eisenberg, *Macromolecules*, 29, 6359 (1996)]. In addition, D. E. Discher and D. Hammer (Pennsylvania University in USA) proposed a novel vesicular structure, "polymersome" using poly(ethylene oxide)-poly(ethylethylene) block copolymer [B M Discher, Y Y Won, D. S. Ege, J. C-M. Lee, F. S. Bates, D. E. Discher, D. A. Hammer, *Science*, 284, 113 (1999)].

All the above polymer aggregates use poly(ethylene oxide) as a corona block in consideration that poly(ethylene oxide) is a nonionic polymer without reactivity with in vivo biological molecules and particularly, poly(ethylene oxide) having molecular weight of 5,000 or less can be filtrated at kidney to be discharged to the exterior. Thanks to such an excellent biocompatibility of poly(ethylene oxide), polymer aggregates using poly(ethylene oxide) have been extensively considered as a polymer material for drug delivery system. In particular, because poly(ethylene oxide) inhibits protein adsorption, polymer aggregation can be prevented from interaction with in vivo molecules in blood, thereby can be protected from removal by immunocytes such as mononuclear phagocyte system (MPS) and can stay in blood for a long time.

However, poly(ethylene oxide) does not have other functional groups except terminal groups, so to be limited to attach cell-adhesion molecules in application of a targetable drug delivery system. In addition, in application of oral or percutaneous administration, it is difficult to increase penetration into the tissue due to a large hydrodynamic volume of poly(ethylene oxide). Besides, there is a limitation in forming various structures of polymer aggregates. In addition, there is defect that block length has to be longer for forming polymer aggregates in comparison with ionic polymers, so that the volume of core part to contain drug is relatively small. Therefore, there have been needs for novel polymer aggregates using another polymers different from poly(ethylene oxide), depending on drug administration routes.

Aggregates formed from polymer electrolytes have been applied as a gene delivery carrier. However, electric charge of the polymer is used in coupling between a polymer and a gene, and therefore, it does not determine surface property of the aggregates.

Adi Eisenberg et al. (McGill University, Canada) reported various structures having a charged hydrophilic polymer as a corona block, wherein the charged polymer exists on the surface of the self-assembled aggregates. He employed polystyrene as a hydrophobic block and poly(acrylic acid) as a hydrophilic block. In this case, polymer aggregates can be formed from poly(acrylic acid) having much lower molecular weight compared with the conventional corona block such as poly(ethylene oxide). This structure is named as "crew-cut" polymer aggregates [L. Zhang and A. Eisenberg, *Science*, 268, 1728 (1995); L. Zhang, K. Yu, A. Eisenberg, *Science*, 272, 1777 (1996); L. Zhang and A. Eisenberg, *Macromolecules*, 29, 8805 (1996)]. In this case, the length of hydrophobic blocks can be controlled to be relatively longer and various types of structures can be formed depending on block length or molecular weight of polymer, condition of aqueous milieu, etc. [C. Allen, D. Maysinger, A. Eisenberg, *Colloids and Surfaces B: Biointerfaces*, 16, 3 (1999)]. However, polystyrene is not a biocompatible polymer and has difficulty in removal after injection into the body.

Therefore, a biocompatible polymer is required in order to be applied as a drug delivery system. Biocompatible polymers must not cause in vivo inflammation or immune reaction, must be biodegraded in vivo to be easily removed, and degradation products thereof must be harmless in vivo. As a polymer satisfying these conditions, biodegradable aliphatic polyesters using lactic acid or glycolic acid as monomer units were approved by FDA. Aliphatic polyester has been extensively used as a drug delivery carrier or a surgical suture, and has been verified biocompatible.

Under this circumstances, in order to solve the above-mentioned problems, the present inventors have conducted extensive studies on novel polymer aggregates using other polymer different from poly(ethylene oxide) as a hydrophilic block. As a result thereof, they found that polymer aggregates comprising cationic polyethylenimine as a hydrophilic block and an aliphatic polyester with biodegradability and biocompatibility as a hydrophobic block can satisfy the above object.

SUMMARY OF THE INVENTION

Therefore, one object of the present invention is to provide biodegradable block copolymers comprising polyethylenimine as a hydrophilic block and aliphatic polyesters as a hydrophobic block and to provide polymer aggregates formed therefrom.

Another object of the present invention is to provide multifunctional block copolymers to be applied in vivo utilizing electric charges and functional group of hydrophilic block.

These and other objects and advantages of the present invention will become apparent to the skilled in the art from the following detailed description as considered in conjunction with the accompanying drawings.

B is a result for polyethylenimine-poly(D,L-lactide-co-glycolide) (Ex. 3); and

C is a result for polyethylenimine-poly(D,L-lactide-co-glycolide) (Ex. 4).

Figure 5:
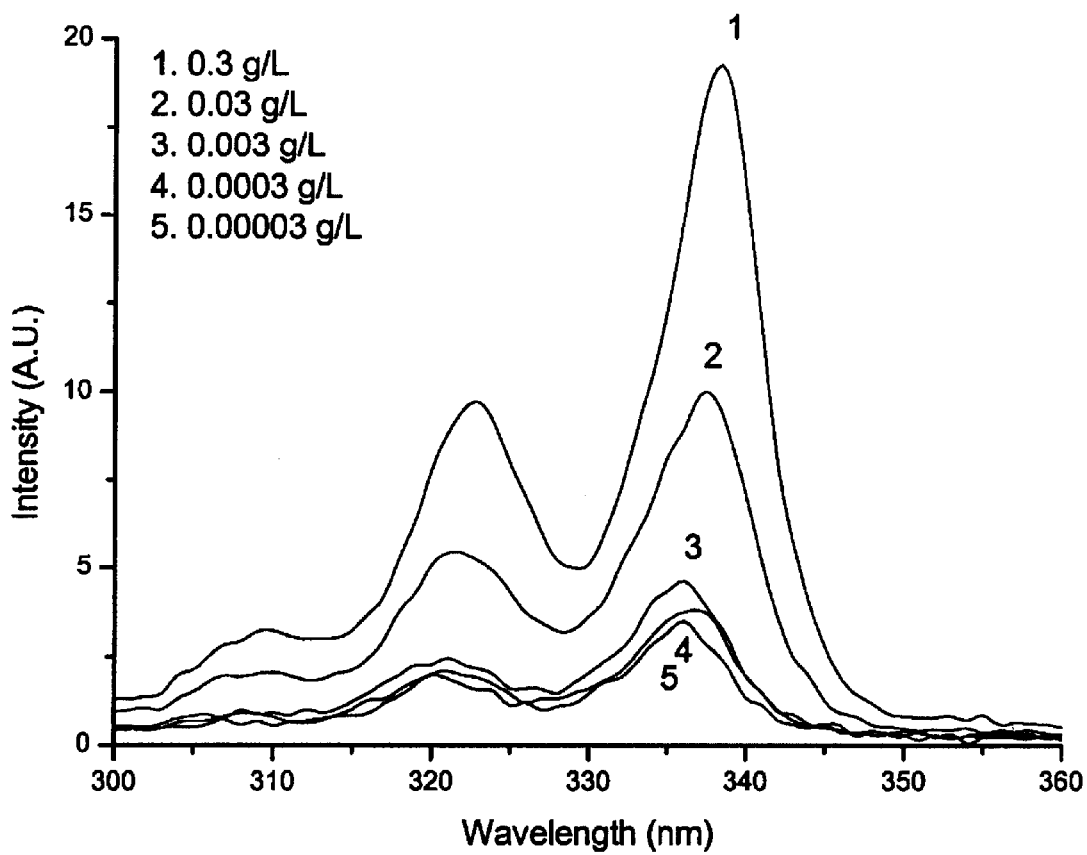

FIG. 5 is a pyrene fluorescence spectrum of each concentration of the aggregates depending on wavelength in aqueous solution of the linear polyethylenimine (Mn=400)-poly(D,L-lactide-co-glycolide) (Mn=25,000) prepared in Example 3.

Figure 6:
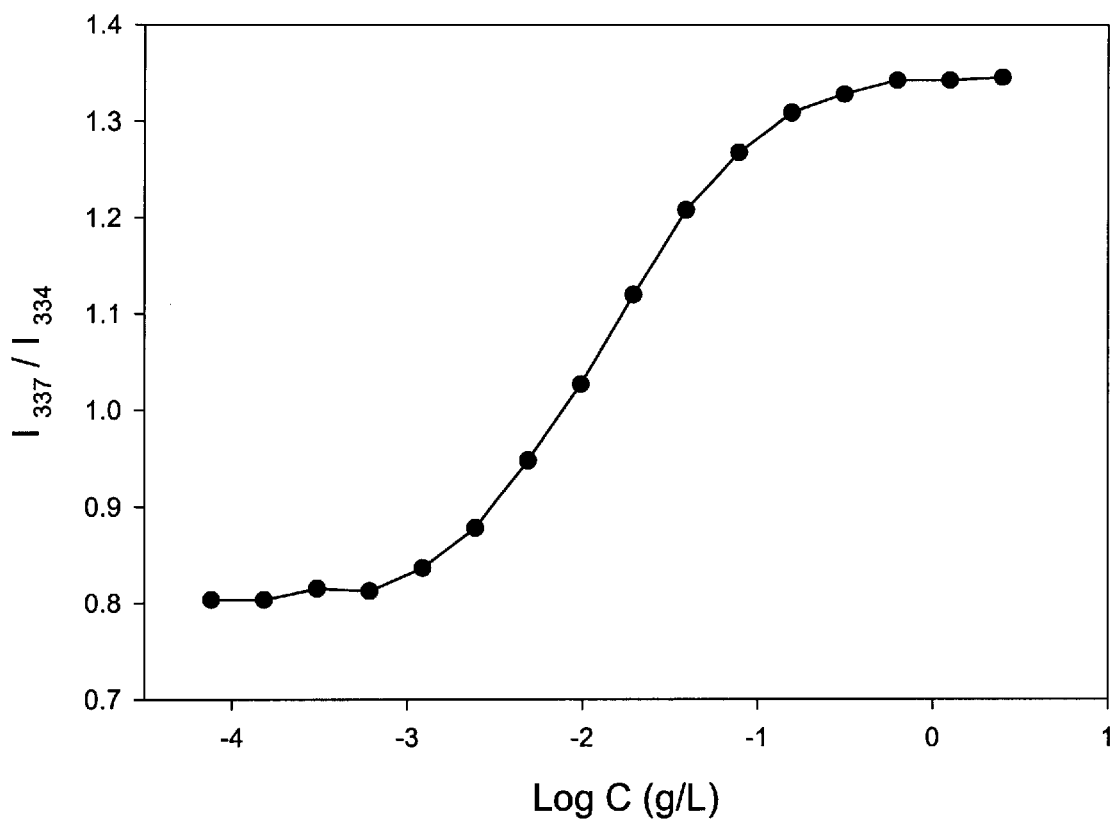

FIG. 6 is ratios of fluorescence intensities at 337 nm and at 334 nm depending on concentrations of the aggregates in aqueous solution of the linear polyethylenimine (Mn=400)-poly(D,L-lactide-co-glycolide) (Mn=25,000) prepared in Example 3.

Figure 7:
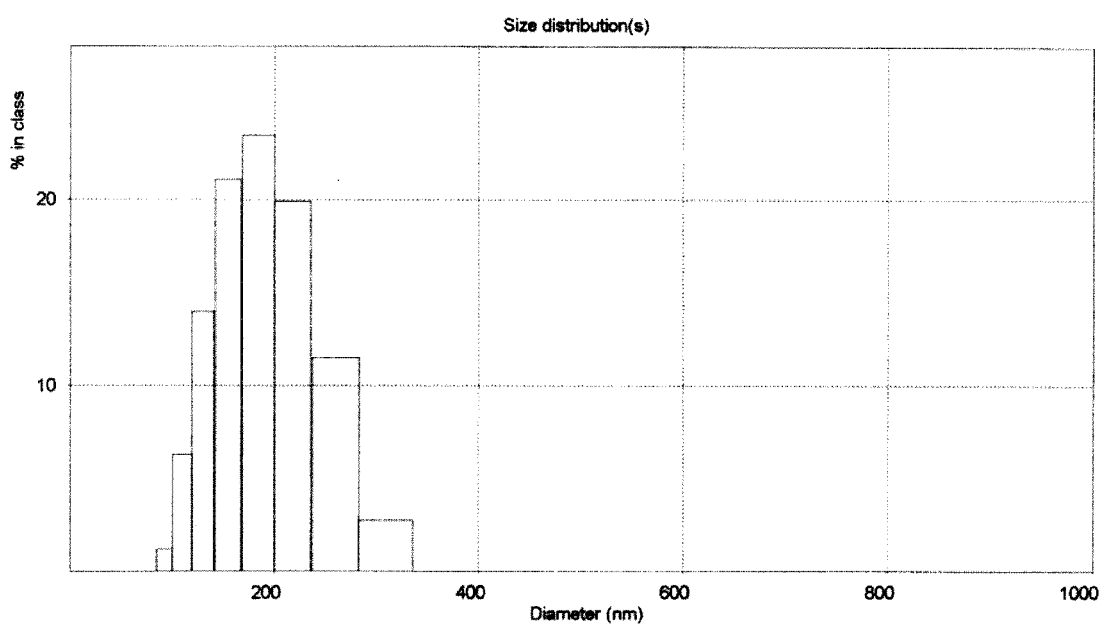

FIG. 7 is a result of dynamic light scattering analysis for the aggregates of the linear polyethylenimine (Mn=400)-poly(D,L-lactide-co-glycolide) (Mn=25,000) prepared in Example 3.

Figure 8:
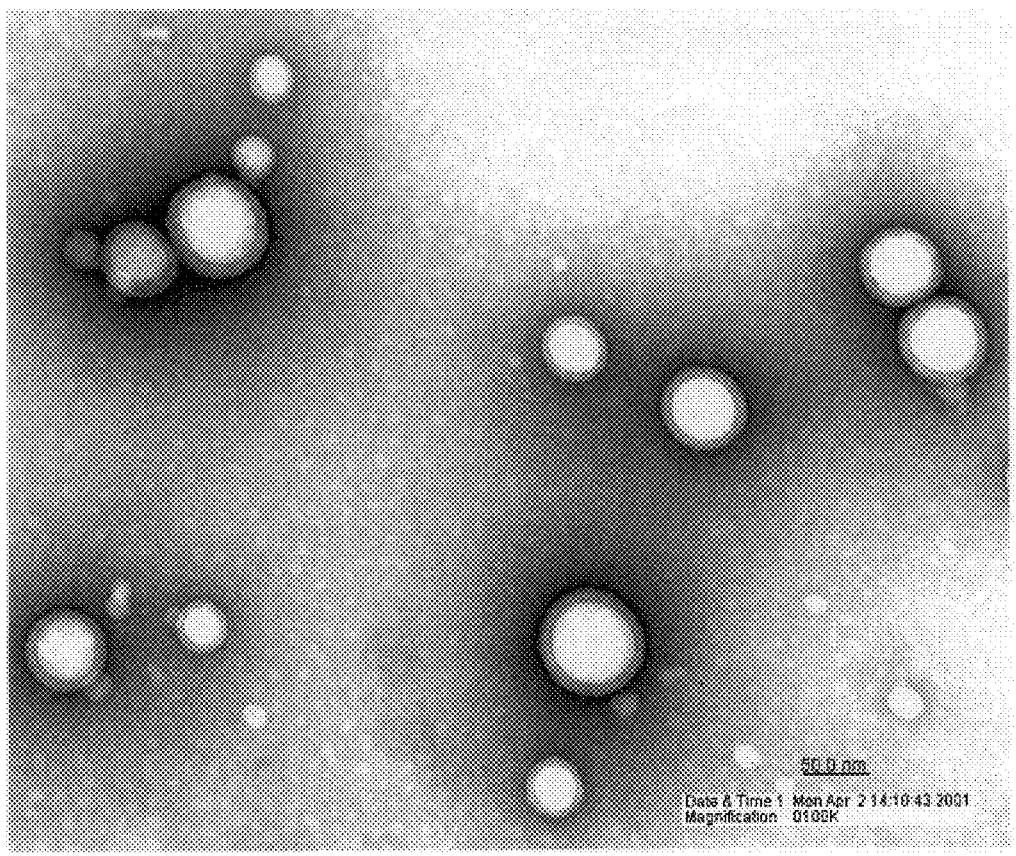

FIG. 8 is a result of transmission electron microscopy (TEM) analysis for the aggregates of the linear polyethylenimine (Mn=400)-poly(D,L-lactide-co-glycolide) (Mn=25,000) prepared in Example 3.

DETAILED DESCRIPTION OF THE INVENTION

The following is a detailed description of the present invention.

The present invention is characterized in that block copolymers comprise a cationic polymer and a biodegradable polymer. More particularly, the present invention is characterized in that block copolymers comprise cationic polyethylenimine (PEI) as a hydrophilic block and biodegradable aliphatic polyester as a hydrophobic block. Further, the present invention provides self-assembled polymer aggregates formed from said block copolymers in an aqueous solution.

In this specification, the term "polymer" refers to a synthetic macromolecule and oligomer, and the term "polymer aggregate" refers to a structure formed by self-assembly of polymer, for example, nanoparticles, micelles, vesicles, cylinders, etc.

Said biodegradable aliphatic polyester employed as a hydrophobic block may be one selected from the group consisting of poly(L-lactide), poly(D,L-lactide), poly(D- lactide-co-glycolide), poly(L-lactide-co-glycolide), poly(D,L-lactide-co-glycolide), polycaprolactone, polyvalerolactone, polyhydroxybutyrate, polyhydroxyvalerate, poly(1,4-dioxan-2-one), polyorthoester and copolymers therebetween.

Poly(D,L-lactide-co-glycolide) (PLGA) may be preferably selected, because biodegradable polymer having various degradation rate can be obtained by controlling monomer ratio of lactic acid and glycolic acid or by controlling polymerization conditions.

Further, said block copolymer can be obtained by covalent bond between polyethylenimine and aliphatic polyester, for example, ester bond, anhydride bond, carbamate bond, carbonate bond, imine or amide bond, secondary amine bond, urethane bond, phosphodiester bond or hydrazone bond. In addition, it may be A-B type of double blocks wherein A is said hydrophobic block of aliphatic polyester and B is said hydrophilic block of polyethylenimine.

In said block copolymer, weight ratio of aliphatic polyester and polyethylenimine may be preferably in a range of 100:1~1:10. If the amount of polyester is excessive, the block copolymer cannot form stable aggregates and thereby precipitated. If the amount of polyethylenimine is excessive, core part to contain drug decreases. Accordingly, it may be preferable to limit the ratio in said range.

Said biodegradable polymer may be employed regardless of molecular weights. Preferably, said biodegradable hydrophobic polyester having 1,000~70,000 of weight average molecular weight (Mw) may be employed. As for said polyethylenimine, it may be effective in forming aggregates to employ hydrophilic polymer of which Mw is 100~10,000.

As a method for forming polymer aggregates in aqueous phase by using biodegradable block copolymers proposed by the present invention, there are a method wherein said block copolymers are directly dispersed in aqueous phase and then ultrasonic wave is irradiated; a method wherein said block copolymers are dispersed or dissolved in organic solvent and then the solvent is extracted with excess of distilled water or evaporated; a method wherein said block copolymers are dispersed or dissolved in organic solvent and then the solvent is evaporated by strongly stirring with a homogenizer or a high-pressure homo-mixer; a method wherein said block copolymers are dispersed or dissolved in organic solvent and then is dialyzed with excess of distilled water; and a method wherein said block copolymers are dispersed or dissolved in organic solvent and then distilled water is added thereto.

In detail, the method for preparing polymer aggregates according to the present invention comprises the following steps of:

(1) dissolving or dispersing said block copolymers in organic solvent and then adding distilled water thereto, to induce phase separation of polymers;

(2) forming aggregates from the block copolymer solution or dispersion of said step (1) by any one method selected from the group consisting of aqueous addition; solvent evaporation; dialysis; phase transition precipitation; ultrasonic irradiation; heating method; stirring method; high-pressure homogenization; and combination therebetween; and (3) filtrating said block copolymer solution or dispersion and then freeze drying to give block copolymer powder.

An organic solvent employed in preparing polymer aggregates by using the present biodegradable block copolymer in aqueous phase may be one or more selected from the group consisting of acetone, dimethylsulfoxide, dimethylformamide, N-methylpyrrolidone, dioxane, tetrahydrofuran, ethyl acetate, acetonitrile, methylethyl ketone, methylene chloride, chloroform, methanol, ethanol, ethyl ether, diethyl ether, hexane and petroleum ether.

In case of pharmaceutical or cosmetic application, it may be preferable to limit the size of said aggregates in a range of 10~1,000 nm, in consideration of penetration into the skin and loading of active ingredients.

The nano-scale polymer aggregates obtained in the present invention have very low critical micelle concentration, approximately 0.1~10 mg/l and are extraordinarily stable in aqueous phase, in comparison with low-molecular-weight micelles. These characteristics enable the present polymer aggregates to maintain their structures in aqueous phase or in vivo after long-term preservation. Therefore, the present polymers have good property as a drug delivery vehicle.

Although said polyethylenimine is classified into linear polymer and branched polymer, it can form polymer aggregates regardless of its structures. The range of molecular weight of polyethylenimine depends on the molecular weight of biodegradable polyesters selected. In general, it may be preferable to employ polyethylenimine having 5,000 or less of molecular weight.

PREFERRED EMBODIMENT OF THE INVENTION

The present invention will be described in more detail by way of the following examples, which should not be considered to limit the scope of the present invention.

<EXAMPLE 1>

Linear Polyethylenimine(Mn=400)-poly(D,L-lactide-co-glycolide) (Mn=11,000) Block Copolymer (carbamate bond)

50 ml of dimethylformamide and 145 mg of N,N-carbonyldiimidazole (CDI) were introduced into the reactor and then stirred uniformly. Thereto was added 5 g of poly(D,L-lactide-co-glycolide) (RG502, Boehringer Ingelheim, Germany), to activate its terminal hydroxy group. To said solution was added 500 mg of linear polyethylenimine(number-average molecular weight: Mn=400) and then, stirred under condition of 1 atm and room temperature. After 12 hours, the resultant was filtrated with nylon filter with 0.45 μm of pore, and then dispersed in tertiary distilled water to remove residue reactant and reagent by dialysis.

Molecular-weight distribution of the obtained polymer was analyzed by gel permeation chromatography. The result confirmed that the obtained polymer exhibits single distribution of molecular weight.

Figure 1A:
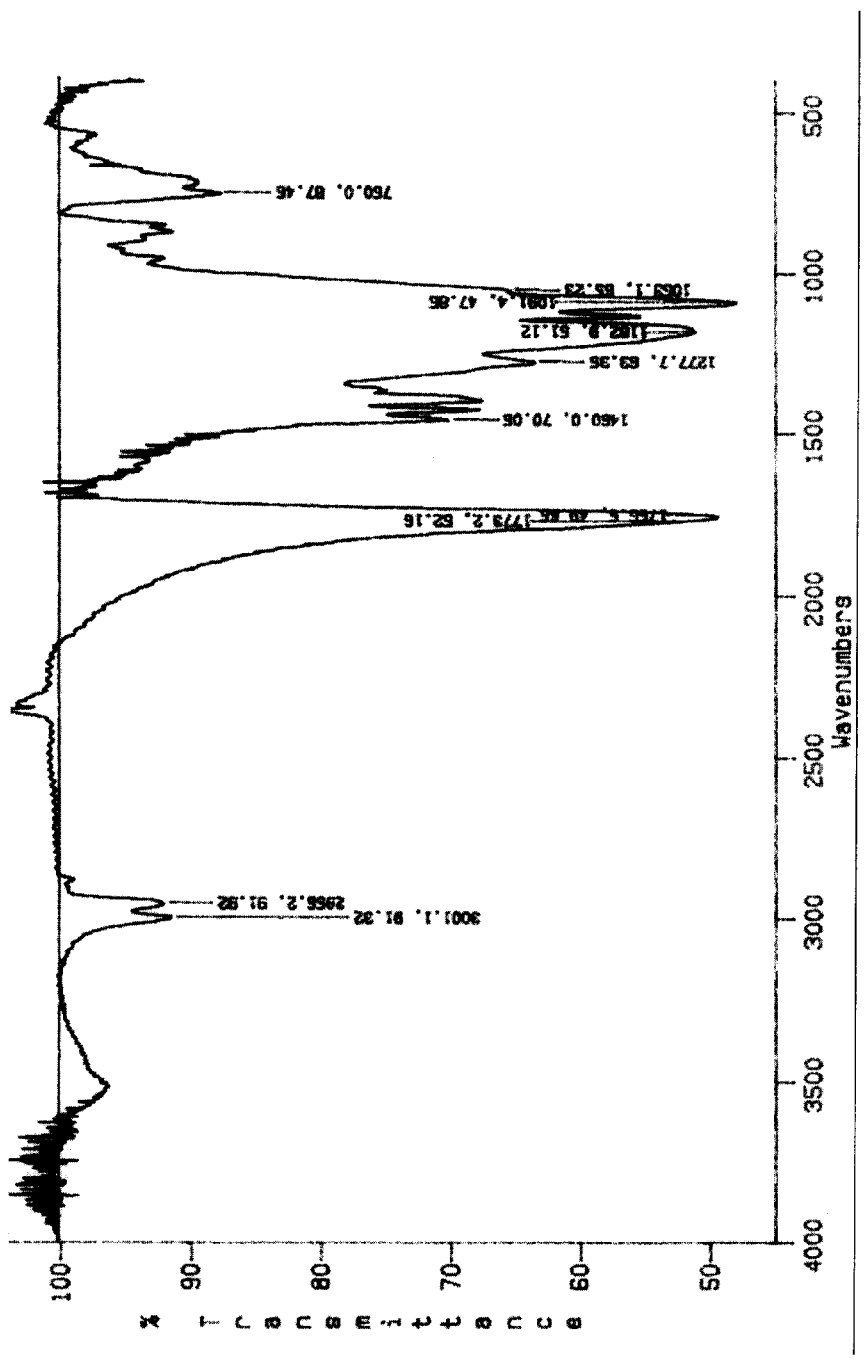
FIG. 1a is an infrared spectrum of typical poly(D,L-lactide-co-glycolide) (Mn=11,000).
Figure 1B:
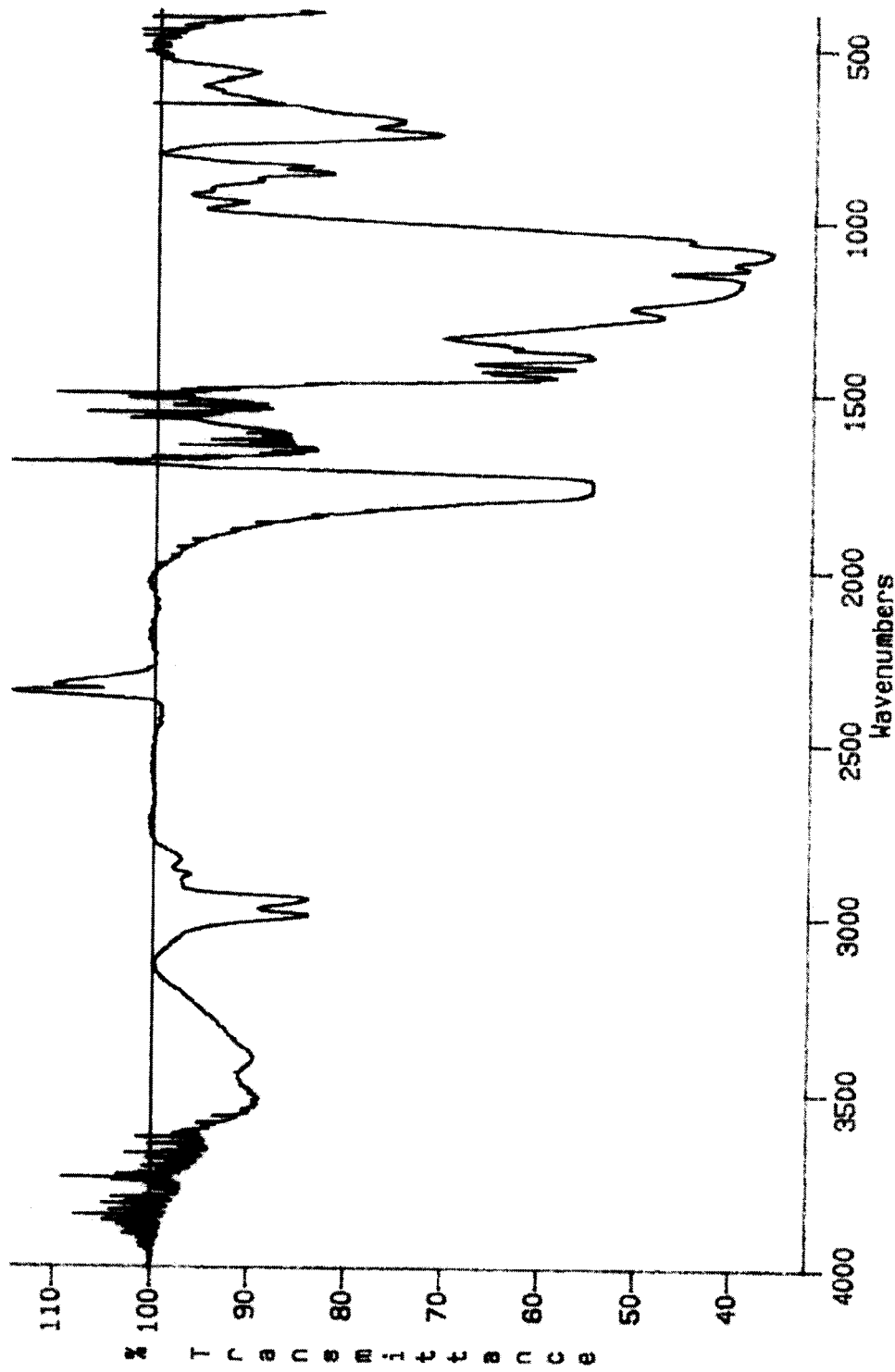
FIG. 1b is an infrared spectrum of the linear polyethylenimine (Mn=400)-poly(D,L-lactide-co-glycolide) (Mn=11,000) block copolymer prepared in Example 1.

Specific peaks of amine and ester were analyzed by means of infrared spectroscope. The results are shown in FIG. 1.

Figure 2:
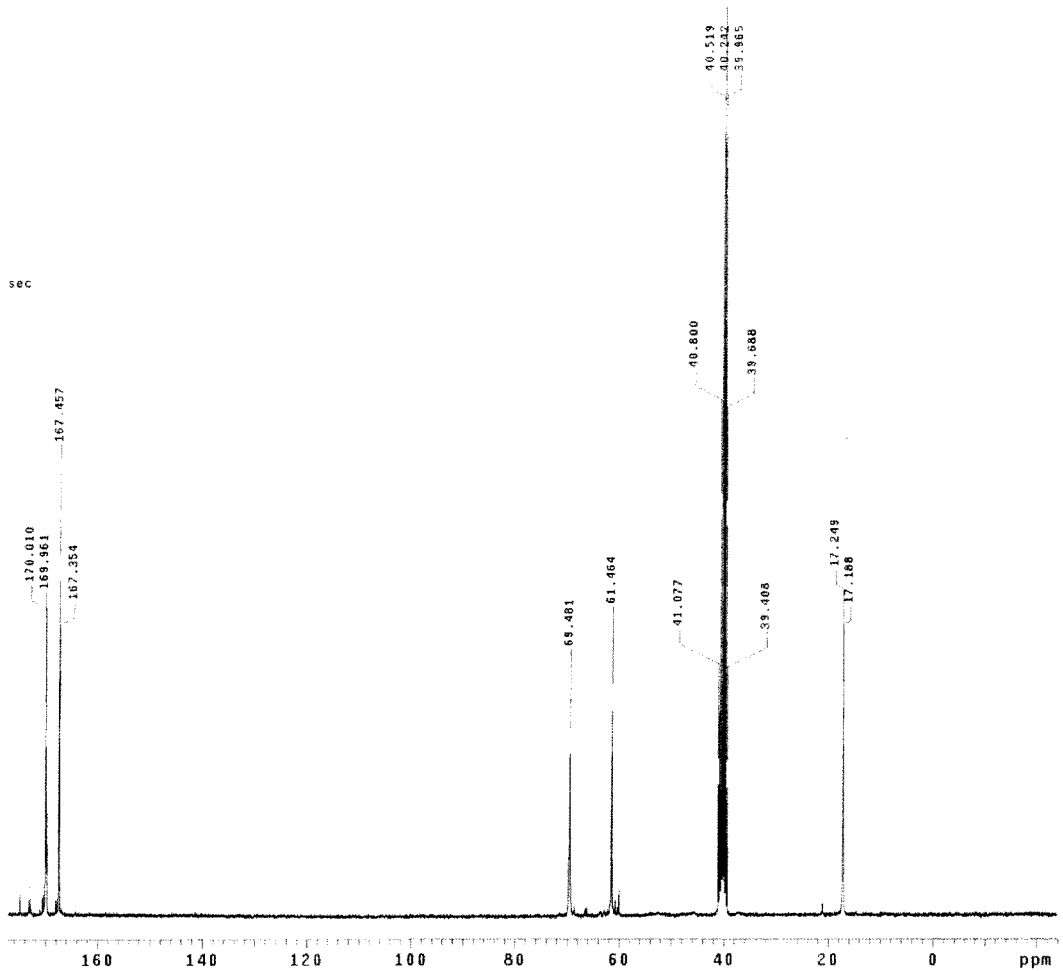
FIG. 2 is a carbon nuclear magnetic resonance ($^{13}$C NMR) spectrum (in deuterated dimethylsulfoxide) of the linear polyethylenimine (Mn=400)-poly(D,L-lactide-co-glycolide) (Mn =11,000) block copolymer prepared in Example 1.

Identification of the obtained polymer was analyzed by carbon nuclear magnetic resonance spectroscopy in deuterated dimethylsulfoxide. The result is shown in FIG. 2. The result identified the obtained polymer as polyethylenimine (PEI)-poly(D,L-lactide-co-glycolide) copolymer.

Thermal property of the polymer was analyzed by means of differential scanning calorimetry (DSC2010, TA Instruments). Heating was performed by 10° C. per minute in a range of −100~100° C. Glass transition temperature(Tg) was determined by exothermal curve output in the secondary heating. Tg of pure poly(D,L-lactide-co-glycolide) before reaction is 42.2° C. and Tg of the linear polyethylenimine (Mn=400)-poly(D,L-lactide-co-glycolide) (Mn=11,000) prepared in this example is 31.75° C.

<EXAMPLE 2>

Branched Polyethylenimine(Mn=600)-poly(D,L-lactide-co-glycolide) (Mn=11,000) block copolymer (carbamate bond)

50 ml of Dimethylformamide and 145 mg of N,N-carbonyldiimidazole were introduced into the reactor and then stirred uniformly. Thereto was added 5 g of poly(D,L-lactide-co-glycolide) (RG502), to activate its terminal hydroxy group. To said solution was added 500 mg of branched polyethylenimine(Mn=600) and then, stirred under condition of 1 atm and room temperature. After 12 hours, the resultant was filtrated with nylon filter with 0.45 μm of pore, and then dispersed in tertiary distilled water to remove residue reactant and reagent by dialysis.

Figure 3:
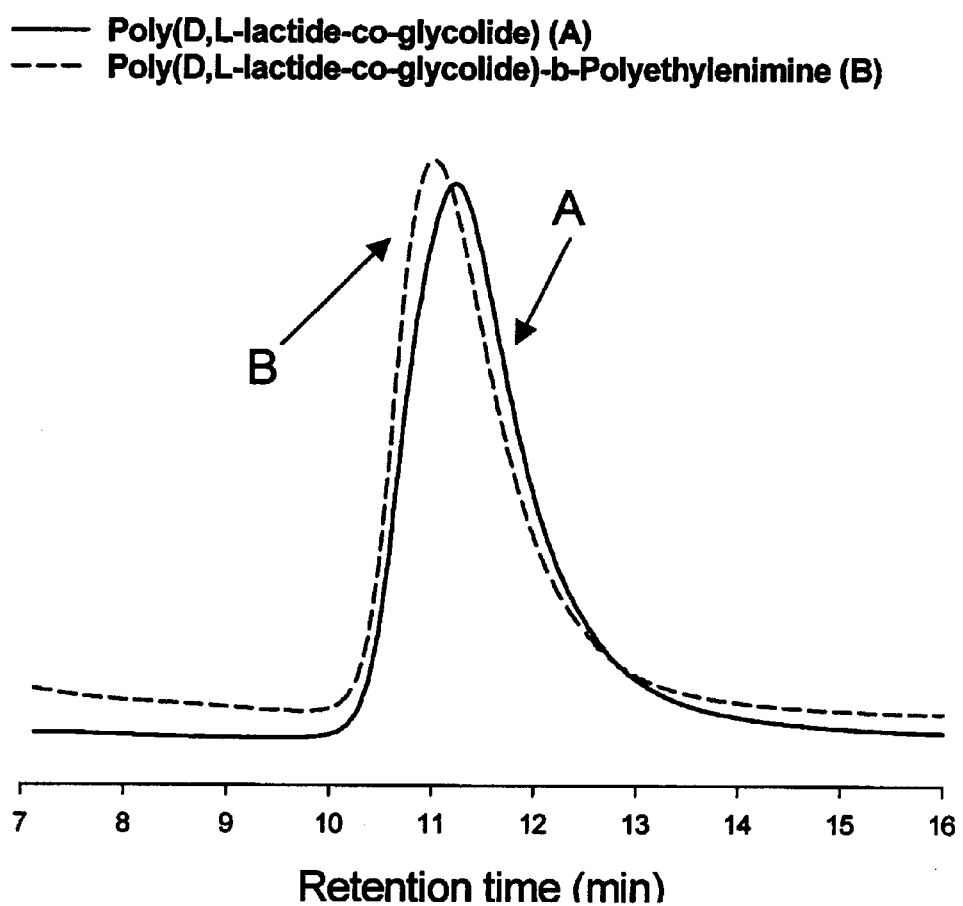
FIG. 3 is a result of gel permeation chromatography (GPC) analysis for the branched polyethylenimine (Mn=600)-poly(D,L-lactide-co-glycolide) (Mn=11,000) block copolymer prepared in Example 2.

As shown in FIG. 3, gel permeation chromatography analysis confirmed that the obtained polymer exhibits single distribution of molecular weight.

Specific peaks of amine and ester were analyzed by means of infrared spectroscope, and identification of the obtained polymer was analyzed by carbon nuclear magnetic resonance spectroscopy in deuterated dimethylsulfoxide. The results identified the obtained polymer as polyethylenimine-poly-D,L-lactide-co-glycolide copolymer.

Thermal property of the polymer was analyzed by means of differential scanning calorimetry. Tg of pure poly(D,L-lactide-co-glycolide) before reaction is 42.2° C. and Tg of the branched polyethylenimine(Mn=600)-poly-D,L-lactide-co-glycolide (Mn=11,000) prepared in this example is 37.6° C.

<EXAMPLE 3>

Linear Polyethylenimine(Mn=400)-poly(D,L-lactide-co-glycolide) (Mn=25,000 ) Block Copolymer (Amide Bond)

100 ml of Dimethylformamide, 123 mg of dicyclohexyl carbodiimide (DCC) and 70 mg of N-hydroxysuccinimide (NHS) were introduced into the reactor and then stirred uniformly. Thereto was added 5 g of poly(D,L-lactide-co-glycolide) (RG503H), to activate its terminal hydroxy group. To said solution was added 0.8 g of linear polyethylenimine(Mn=400) and then, stirred under condition of 1 atm and room temperature. After 12 hours, the resultant was filtrated with nylon filter with 0.45 μm of pore, and then dispersed in tertiary distilled water to remove residue reactant and reagent by dialysis.

Gel permeation chromatography analysis confirmed that the obtained polymer exhibits single distribution of molecular weight.

Specific peaks of amine and ester were analyzed by means of infrared spectroscope, and identification of the obtained polymer was analyzed by carbon nuclear magnetic resonance spectroscopy in deuterated dimethylsulfoxide. The results identified the obtained polymer as polyethylenimine-poly-D,L-lactide-co-glycolide copolymer.

Figure 4:
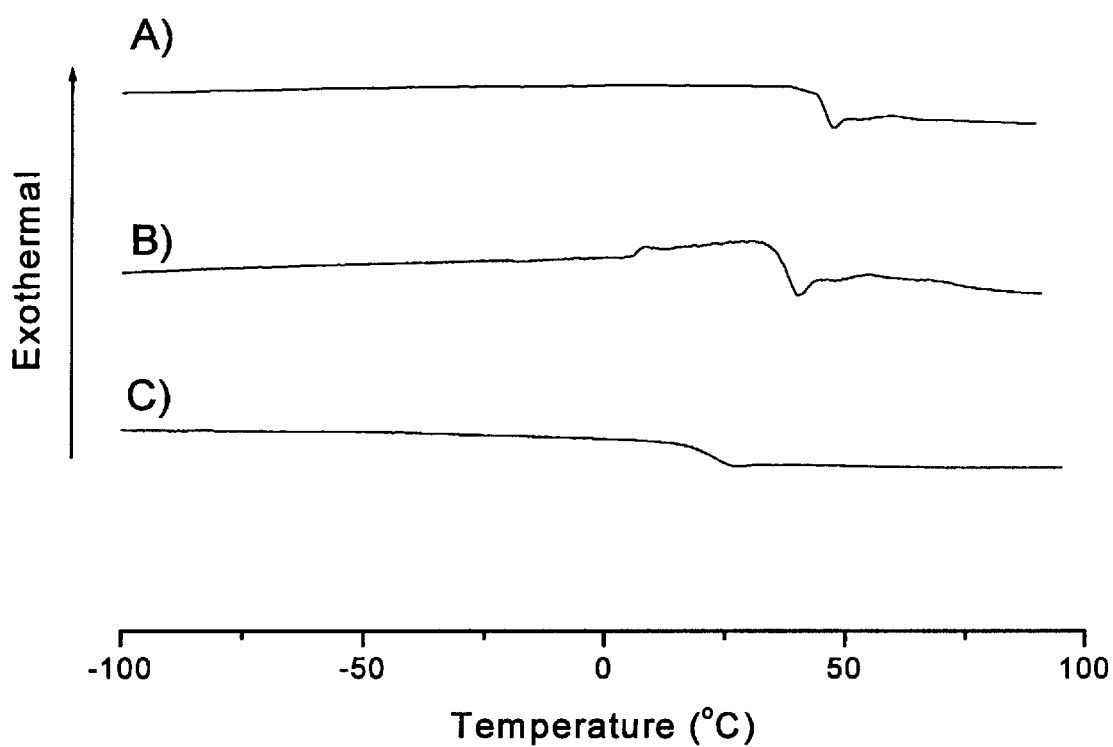
FIG. 4 is results of differential scanning calorimetry (DSC) analysis for the linear and the branched polyethylenimine-poly(D,L-lactide-co-glycolide) block copolymers prepared in Examples 3 and 4, respectively, wherein, A is a result for poly(D,L-lactide-co-glycolide)

Thermal property of the polymer was analyzed by means of differential scanning calorimetry. As shown in FIG. 4, Tg of pure poly-D,L-lactide-co-glycolide before reaction is 43.9° C. and Tg of the linear polyethylenimine (Mn=400)-poly(D,L-lactide-co-glycolide) (Mn=25,000) prepared in this example is 37.6° C.

<EXAMPLE 4>

Branched Polyethylenimine(Mn=600)-poly(D,L-lactide-co-glycolide) (Mn=25,000) Block Copolymer (amide bond)

100 ml of Dimethylformamide, 123 mg of dicyclohexyl carbodiimide and 70 mg of N-hydroxysuccinimide were introduced into the reactor and then stirred uniformly. Thereto was added 5 g of poly(D,L-lactide-co-glycolide) (RG503H), to activate its terminal hydroxy group. To said solution was added 0.8 g of branched polyethylenimine (Mn=600) and then, stirred under condition of 1 atm and room temperature. After 12 hours, the resultant was filtrated with nylon filter with 0.45 μm of pore, and then dispersed in tertiary distilled water to remove residue reactant and reagent by dialysis.

Gel permeation chromatography analysis confirmed that the obtained polymer exhibits single distribution of molecular weight.

Specific peaks of amine and ester were analyzed by means of infrared spectroscope, and identification of the obtained polymer was analyzed by carbon nuclear magnetic resonance spectroscopy in deuterated dimethylsulfoxide. The results identified the obtained polymer as polyethylenimine-poly-D,L-lactide-co-glycolide copolymer.

Thermal property of the polymer was analyzed by means of differential scanning calorimetry. As shown in FIG. 4, Tg of pure poly-D,L-lactide-co-glycolide before reaction is 43.9° C. and Tg of the branched polyethylenimine (Mn=600)-poly(D,L-lactide-co-glycolide) (Mn=25,000) prepared in this example is 20.25° C.

<EXAMPLE 5 >

Preparation of Polymer Aggregates 25 mg of each sample of the block copolymers prepared in Examples 1~4 was uniformly dispersed in 0.5 ml of acetone and then gradually added into 10 ml of tertiary distilled water under stirring. Each sample was evaporated in chemical hood for 12 hours to remove acetone. Subsequently, each sample was diluted with deionized and tertiary distilled water to a concentration range of 2.5 g/l~0.0001 g/l, in detail, 2.5 g/l, $6.25 \times 10^{-1}$ g/l, $3.13 \times 10^{-1}$ g/l, $1.56 \times 10^{-1}$ g/l, $7.81 \times 10^{-2}$ g/l, $3.91 \times 10^{-2}$ g/l, $1.95 \times 10^{-2}$ g/l, $9.77 \times 10^{-3}$ g/l, $4.88 \times 10^{-3}$ g/l, $2.44 \times 10^{-3}$ g/l, $1.22 \times 10^{-3}$ g/l, $6.10 \times 10^{-4}$ g/l, $3.05 \times 10^{-4}$ g/l, $1.53 \times 10^{-4}$ g/l, and $7.63 \times 10^{-5}$ g/l.

Critical micelle concentration was measured by fluorescence peak analysis of pyrene. Firstly, pyrene was dissolved in acetone to give $6 \times 10^{-7}$ M of solution. The solution was introduced into eppendrof tube by 1 ml per tube. The acetone was evaporated in chemical hood for 12 hours to be removed. Into the eppendrof tube was added said 2.5 g/l~0.0001 g/l of polymer aggregates solution and then stood at a temperature of 37° C. for 4 hours. Fluorescence peak analyzer was Hitachi F-4500 (Nissei Sangyo Co., Ltd, Tokyo, Japan). Slit spacing was 5 at both excitation and emission, scanning velocity was 240 nm/min, and PMT voltage was 400V. Emission wavelength was fixed at 390 nm and excitation wavelength was scanned from 300 nm to 360 nm. The pyrene fluorescence spectrum of each concentration of the aggregates is shown in FIG. 5. Critical micelle concentration was determined by ratios of fluorescence intensities at 337 nm and at 334 nm($I_{337nm}/I_{334nm}$) depending on concentrations of the micelle, as shown in FIG. 6.

Average particle diameters of the polymer aggregates prepared in Examples 1~4 were obtained by dynamic light scattering (DLS) analysis, as shown in FIG. 7. The concentration of the aggregates was 0.6 mg/ml and scattering angle was fixed at 90°.

The critical micelle concentration, the average particle diameter and the dispersivity of the polymer aggregates are shown in Table 1.

TABLE 1

|  | Critical micelle concentration (mg/l) | Average particle diameter (nm) | Dispersivity |
|---|---|---|---|
| Ex. 1 | 2.54 | 188.3 | 0.10 |
| Ex. 2 | 1.45 | 161.1 | 0.12 |
| Ex. 3 | 1.54 | 166.2 | 0.11 |
| Ex. 4 | 2.17 | 136.7 | 0.14 |

Morphology of the polymer aggregates prepared in Examples 1~4 was analyzed by means of transmission electron microscopy(TEM, JEOL 2010). The sample was put on 100 mesh of copper grid coated with carbon, and dyed with 2% of uranyl acetate solution. Magnification was 1,000,000. The result is shown in FIG. 8.

As shown by the above results, the present amphiphilic biodegradable block copolymers comprising biodegradable aliphatic polyester as a hydrophobic block and polyethylenimine as a hydrophilic block have particle properties as above-described, so to be employed as appropriate vehicles in forming structures to load water-soluble or hydrophobic drug within inner core or hydrophobic region.

As confirmed by the above description, the polyethylenimine-polyester block copolymers according to the present invention can form various size of polymer aggregates and have very low critical micelle concentration, approximately 0.001~0.005 g/l. And, the transmission electron microscopy analysis confirmed that the polymer aggregates are sphere. Therefore, the present block copolymers can form structures capable of loading water-soluble or hydrophobic drug within inner core or hydrophobic region. The polymer aggregates formed from the present block copolymers are expected to accelerate solubilization of insoluble drug and oral or percutaneous penetration, and to be applied as delivery vehicle of protein, gene or drug having electric charge.

Although preferred embodiments of the present invention have been described in detail hereinabove, it should be clearly understood that many variations of the basic inventive concepts herein taught which may appear to those skilled in the art will still fall within the spirit and scope of the present invention as defined in the appended claims.

What is claimed is:

1. Amphiphilic biodegradable block copolymer comprising a biodegradable aliphatic polyester as a hydrophobic block and polyethylenimine as a hydrophilic block.

2. The block copolymer according to claim 1, wherein said biodegradable aliphatic polyester is one or more selected from the group consisting of poly(L-lactide), poly(D,L-lactide), poly(D-lactide-co-glycolide), poly(L-lactide-co-glycolide), poly(D,L-lactide-co-glycolide), polycaprolactone, polyvalerolactone, polyhydroxybutyrate, polyhydroxyvalerate, poly(1,4-dioxan-2-one), polyorthoester and copolymers therebetween.

3. The block copolymer according to claim 1, wherein said polyethylenimine and said aliphatic polyester are bonded by a covalent bond that selected from the group consisting of ester bond, anhydride bond, carbamate bond, carbonate bond, imine or amide bond, secondary amine bond, urethane bond, phosphodiester bond and hydrazone bond.

4. The block copolymer according to claim 1, wherein said polyethylenimine and said aliphatic polyester are composed of A-B type of double blocks, wherein A is hydrophobic block of aliphatic polyester and B is hydrophilic block of polyethylenimine.

5. The block copolymer according to claim 1, wherein weight ratio of said aliphatic polyester and said polyethylenimine is in a range of 100:1~1:10.

6. The block copolymer according to claim 1, wherein said aliphatic polyester has 1,000~70,000 of weight-average molecular weight.

7. The block copolymer according to claim 1, wherein said polyethylenimine has 100~10,000 of weight-average molecular weight.

8. A method for preparing amphiphilic block copolymer aggregates, which comprises the following steps of:
(1) dissolving or dispersing amphiphilic biodegradable block copolymers comprising a biodegradable aliphatic polyester as a hydrophobic block and polyethylenimine as a hydrophilic block in organic solvent, and then adding distilled water thereto, to induce phase separation of polymers;
(2) forming aggregates from the block copolymer solution or dispersion of said step (1) by any one method selected from the group consisting of aqueous addition; solvent evaporation; dialysis; phase transition precipitation; ultrasonic irradiation; heating method; stirring method; high-pressure homogenization; and combination therebetween; and
(3) filtrating said block copolymer solution or dispersion and then freeze drying to give block copolymer powder.

9. The method according to claim 8, wherein said organic solvent employed in preparing polymer aggregates is one or more selected from the group consisting of acetone, dimethylsulfoxide, dimethylformamide, N-methylpyrrolidone, dioxane, tetrahydrofuran, ethyl acetate, acetonitrile, methylethyl ketone, methylene chloride, chloroform, methanol, ethanol, ethyl ether, diethyl ether, hexane and petroleum ether.

10. The method according to claim 8, wherein said biodegradable aliphatic polyester is one or more selected from the group consisting of poly(L-lactide), poly(D,L-lactide), poly(D-lactide-co-glycolide), poly(L-lactide-co-glycolide), poly(D,L-lactide-co-glycolide), polycaprolactone, polyvalerolactone, polyhydroxybutyrate, polyhydroxyvalerate, poly(1,4-dioxan-2-one), polyorthoester and copolymers therebetween.

11. The method according to claim 8, wherein said polyethylenimine and said aliphatic polyester are bonded by a covalent bond that selected from the group consisting of ester bond, anhydride bond, carbamate bond, carbonate bond, imine or amide bond, secondary amine bond, urethane bond, phosphodiester bond and hydrazone bond.

12. The method according to claim 8, wherein said polyethylenimine and said aliphatic polyester are composed of A-B type of double blocks, wherein A is hydrophobic block of aliphatic polyester and B is hydrophilic block of polyethylenimine.

13. The method according to claim 8, wherein weight ratio of said aliphatic polyester and said polyethylenimine is in a range of 100:1~1:10.

14. Amphiphilic block copolymer aggregates prepared by dispersing amphiphilic biodegradable block copolymers comprising a biodegradable aliphatic polyester as a hydrophobic block and polyethylenimine as a hydrophilic block in a solvent.

15. The aggregates according to claim 14, of which average particle diameter is in a range of 10~1,000 nm.

16. The aggregates according to claim 14, wherein said biodegradable aliphatic polyester is one or more selected from the group consisting of poly(L-lactide), poly(D,L-lactide), poly(D-lactide-co-glycolide), poly(L-lactide-co-glycolide), poly(D,L-lactide-co-glycolide), polycaprolactone, polyvalerolactone, polyhydroxybutyrate, polyhydroxyvalerate, poly(1,4-dioxan-2-one), polyorthoester and copolymers therebetween.

17. The aggregates according to claim 14, wherein said polyethylenimine and said aliphatic polyester are bonded by a covalent bond that selected from the group consisting of ester bond, anhydride bond, carbamate bond, carbonate bond, imine or amide bond, secondary amine bond, urethane bond, phosphodiester bond and hydrazone bond.

18. The aggregates according to claim 14, wherein said polyethylenimine and said aliphatic polyester are composed of A-B type of double blocks, wherein A is hydrophobic block of aliphatic polyester and B is hydrophilic block of polyethylenimine.

19. The method according to claim 14, wherein weight ratio of said aliphatic polyester and said polyethylenimine is in a range of 100:1~1:10.

* * * * *